United States Patent [19]

DiGuiseppi et al.

[11] Patent Number: 5,264,643
[45] Date of Patent: * Nov. 23, 1993

[54] PROCESS FOR CONVERTING OLEFINS TO HIGHER HYDROCARBONS

[75] Inventors: Frank T. DiGuiseppi, Yardville; Scott Han, Lawrenceville; Roland H. Heck, Pennington, all of N.J.

[73] Assignee: Mobil Oil Corp., Fairfax, Va.

[*] Notice: The portion of the term of this patent subsequent to Aug. 17, 2010 has been disclaimed.

[21] Appl. No.: 987,850

[22] Filed: Dec. 9, 1992

[51] Int. Cl.$^5$ .............................................. C07C 2/02
[52] U.S. Cl. ..................................... 585/533; 585/520; 585/530; 585/532
[58] Field of Search ................. 585/520, 530, 532, 533

[56] References Cited

U.S. PATENT DOCUMENTS

| | | |
|---|---|---|
| 3,960,978 | 6/1976 | Givens et al. . |
| 4,021,502 | 5/1977 | Plank et al. . |
| 4,150,062 | 4/1979 | Garwood et al. . |
| 4,211,640 | 7/1980 | Garwood ............................ 208/255 |
| 4,227,992 | 10/1980 | Garwood et al. ..................... 208/46 |
| 4,439,409 | 3/1984 | Puppe et al. ......................... 423/328 |
| 4,456,779 | 6/1984 | Owen et al. ......................... 585/415 |
| 4,524,232 | 6/1985 | Chester et al. ...................... 585/517 |
| 4,547,612 | 10/1985 | Tabak .................................. 585/533 |
| 4,826,667 | 5/1989 | Zones et al. ........................ 423/277 |
| 4,954,325 | 9/1990 | Rubin et al. ........................ 423/328 |
| 4,956,514 | 9/1990 | Chu .................................... 585/520 |
| 4,981,663 | 1/1991 | Rubin .................................. 423/277 |
| 5,021,141 | 6/1991 | Rubin .................................... 208/46 |
| 5,068,096 | 11/1991 | Valyocsik .......................... 585/520 |
| 5,134,241 | 7/1992 | Le et al. ............................. 585/520 |

FOREIGN PATENT DOCUMENTS 0293032 11/1988 European Pat. Off. .

Primary Examiner—Patrick P. Garvin
Assistant Examiner—E. D. Irzinski
Attorney, Agent, or Firm—Alexander J. McKillop; Malcolm D. Keen; Dennis P. Santini

[57] ABSTRACT

Light olefins are converted to heavier hydrocarbon products, e.g., those boiling in the gasoline, distillate, and/or lube range, under oligomerization reaction conditions in the presence of catalyst comprising zeolite MCM-49.

16 Claims, 5 Drawing Sheets

PROCESS FOR CONVERTING OLEFINS TO HIGHER HYDROCARBONS

BACKGROUND OF THE INVENTION

This invention relates to a process for converting oligomerizable olefins, e.g., $C_2$–$C_{16}$ olefins, to higher molecular weight hydrocarbon products including those boiling in the gasoline, distillate, and lube range over catalyst comprising synthetic porous crystalline MCM-49. The present process provides high conversion, especially for conversion of lower olefins such as propylene, to valuable products useful, as examples, for etherification and as high octane gasoline.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIB element, e.g., aluminum, is balanced by the inclusion in the crystal of a cation, e.g., an alkali metal or an alkaline earth metal cation. This can be expressed wherein the ratio of the Group IIIB element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

U.S. Pat. No. 4,439,409 refers to a composition of matter named PSH-3 and its synthesis from a reaction mixture containing hexamethyleneimine, an organic compound which acts as directing agent for synthesis of the presently used MCM-49. A composition of matter appearing to be identical to the PSH-3 of U.S. Pat. 4,439,409, but with additional structural components, is taught in European Patent Application 293,032. Hexamethyleneimine is also used for synthesis of MCM-22 in U.S. Pat. No. 4,954,325; MCM-35 in U.S. Pat. 4,981,663; and a ZSM-12 material in U.S. Pat. 5,021,141. A composition of matter referred to as zeolite SSZ-25 is taught in U.S. Pat. No. 4,826,667 and European Patent Application 231,860, said zeolite being synthesized from a reaction mixture containing an adamantane quaternary ammonium ion.

Developments in zeolite catalysts and hydrocarbon conversion processes have created interest in utilizing olefinic feedstocks, such as petroleum refinery streams rich in lower olefins, for the production of $C_5+$ gasoline, diesel fuel, lube stocks, etc.

U.S. Pat. No. 4,956,514 discloses conversion of light olefins to heavier hydrocarbons, e.g., gasoline, distillate, and lube boiling range products, over catalyst comprising MCM-22, a crystalline material taught in U.S. Pat. No. 4,954,325.

U.S. Pat. Nos. 3,960,978; 4,021,502; 4,150,062; 4,211,640; 4,227,992; 4,456,779; and 4,547,612 disclose the conversion of $C_2$–$C_5$ olefins, alone or in admixture with paraffinic component(s), into higher hydrocarbons over zeolites having controlled acidity.

U.S. Pat. No. 4,524,232 discloses a combination process for producing high viscosity index lubes from light olefins employing in separate stages a particular pore size zeolite catalyst, e.g., ZSM-23, and another pore size zeolite catalyst, e.g., ZSM-5.

SUMMARY OF THE INVENTION

In accordance with the present invention, a feedstock containing at least one oligomerizable olefin is oligomerized to a product containing oligomerized olefin, e.g., a product containing a substantial quantity of component(s) boiling in the gasoline, distillate and/or lube range, by contacting said olefin with an olefin oligomerization catalyst composition under olefin oligomerization conditions to provide said oligomerization product, the olefin oligomerization catalyst composition comprising a particular, porous crystalline material designated MCM-49, characterized as-synthesized by an X-ray diffraction pattern including interplanar d-spacings at $13.15 \pm 0.26$, $12.49 \pm 0.24$, $11.19 \pm 0.22$, $6.43 \pm 0.12$, $4.98 \pm 0.10$, $4.69 \pm 0.09$, $3.44 \pm 0.07$, and $3.24 \pm 0.06$ Angstroms. The d-spacing maximum at $13.15 \pm 0.26$ Angstroms is observed as a shoulder of the intense peak at $12.49 \pm 0.24$ Angstroms.

As is demonstrated hereinafter, MCM-49 has exceptionally high activity for olefin, e.g., propylene, conversion to higher value products. It is from about 75°–200° C. more active than other crystalline zeolites such as ZSM-5, ZSM-23, ZSM-35, and MCM-22 in achieving 90+% olefin, e.g., propylene, conversion.

DESCRIPTION OF SPECIFIC EMBODIMENTS

Figure 1A:
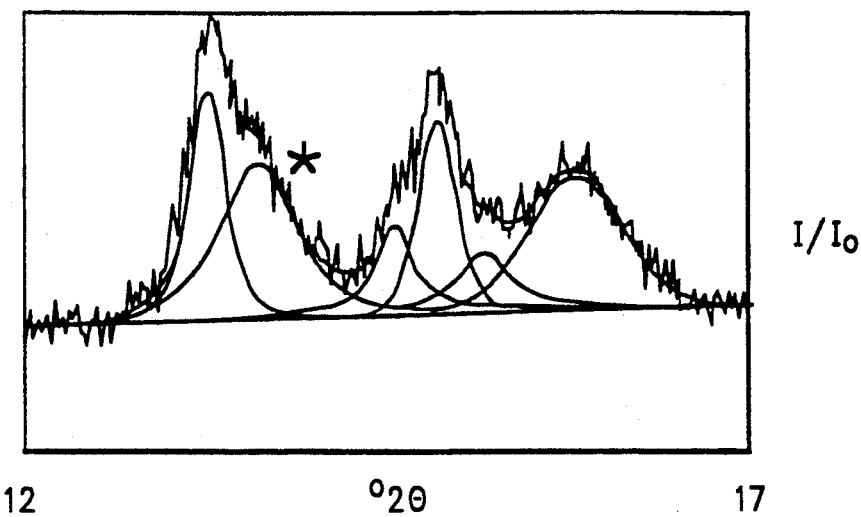
FIG. 1a shows a segment of the X-ray diffraction pattern of the as-synthesized precursor of MCM-22 from a repeat of Example 1 of U.S. Pat. No. 4,954,325.

Any oligomerizable olefin is suitable for use as feedstock in the process of this invention. Suitable olefinic feedstocks can be obtained from a variety of sources including fossil fuel processing streams such as gas separation units, the cracking of $C_2+$ hydrocarbons, coal by-products, and various synthetic fuel processing streams. The cracking of ethane and the conversion of the effluent is disclosed in U.S. Pat. No. 4,100,218 and conversion of ethane to aromatics over Ga-ZSM-5 is disclosed in U.S. Pat. No. 4,350,835. Olefinic effluent from the fluidized catalytic cracking of gas oil, and the like, is a valuable source of olefins, mainly $C_3$–$C_4$ olefins, suitable for conversion according to the present olefin oligomerization process. Olefinic refinery streams can be advantageously converted to valuable higher hydrocarbons employing the catalytic oligomerization process of this invention. One such stream which is advantageously employed as feed herein is an FCC light olefin stream possessing the following typical composition.

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

The crystalline material MCM-49 for use as catalyst component in this invention is described in U.S. patent application Serial No. 07/802,938, entirely incorporated herein by reference, and has a composition involving the molar relationship:

$$X_2O_3:(n)YO_2,$$

wherein X is a trivalent element, such as aluminum, boron, iron and/or gallium, preferably aluminum; Y is a tetravalent element such as silicon, titanium, and/or germanium, preferably silicon; and n is less than about 35, e.g., from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

$$(0.1-0.6)M_2O:(1-4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The crystalline material for use in the invention is thermally stable and in the calcined form exhibits high surface area (greater than 400 m²/gm) and unusually large sorption capacity when compared to previously described materials such as calcined PSH-3 (U.S. Pat. No. 4,439,409) and SSZ-25 (U.S. Pat. No. 4,826,667) having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-49 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason, the precise intensity and position of the 13.15±0.26 Angstroms peak are difficult to determine within the stated range.

In its calcined form, the crystalline MCM-49 material for use in the invention is a single crystal phase with little or no detectable impurity crystal phases having an X-ray diffraction pattern which is not easily distinguished from that of MCM-22, but is readily distinguishable from the patterns of other known crystalline materials. The X-ray diffraction pattern of the calcined form of MCM-49 includes the lines listed in Table II below:

TABLE II

| Interplanar d-Spacing (A) | Relative Intensity, I/Io × 100 |
|---|---|
| 12.41 ± 0.24 | vs |

TABLE II-continued

| Interplanar d-Spacing (A) | Relative Intensity, I/Io × 100 |
|---|---|
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g., MCM-22 and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

Figure 1B:
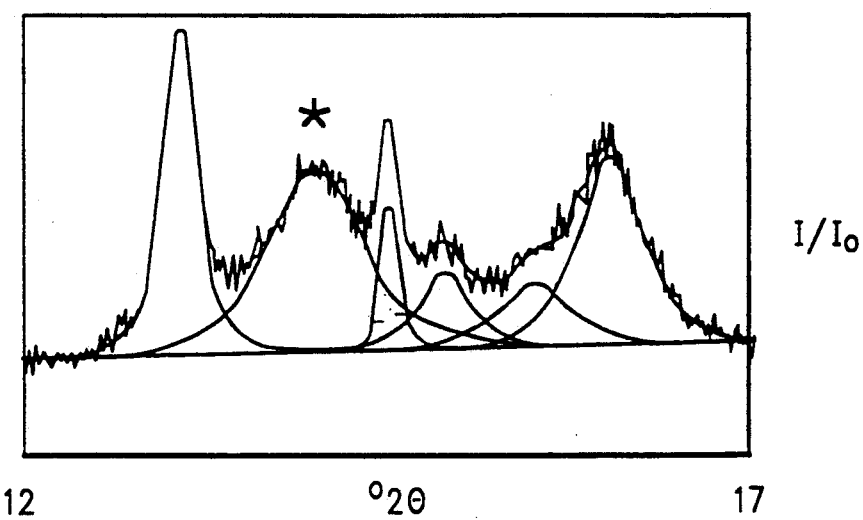
FIG. 1b shows a segment of the X-ray diffraction pattern of the as-synthesized crystalline material product of Example 7, hereinafter presented.
Figure 1C:
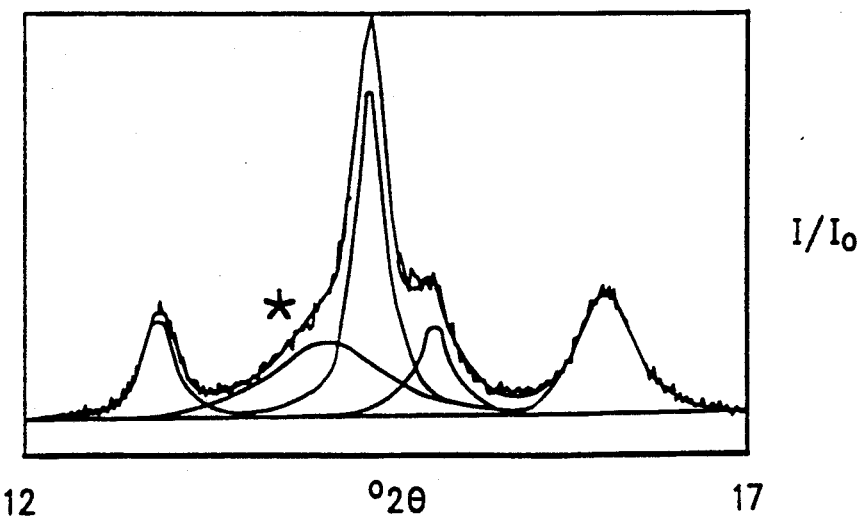
FIG. 1c shows a segment of the X-ray diffraction pattern of the calcined MCM-22 from a repeat of Example 1 of U.S. Pat. No. 4,954,325.

The present as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and ~6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. Unfortunately, the ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak. FIG. 1 shows the same segment of the diffraction patterns of precursor MCM-22, calcined MCM-22, and MCM-49; the position of the ~6.6–6.3 Angstroms peak is indicated in each segment by an asterisk. Because the ~6.4 Angstroms peak is unobscured in MCM-49, it was chosen as a better means of distinguishing MCM-49 from the calcined forms of MCM-22 and PSH-3 rather than the much stronger ~12.8 Angstroms peak. Table I lists all diffraction peaks characteristic of MCM-49.

Figure 8:
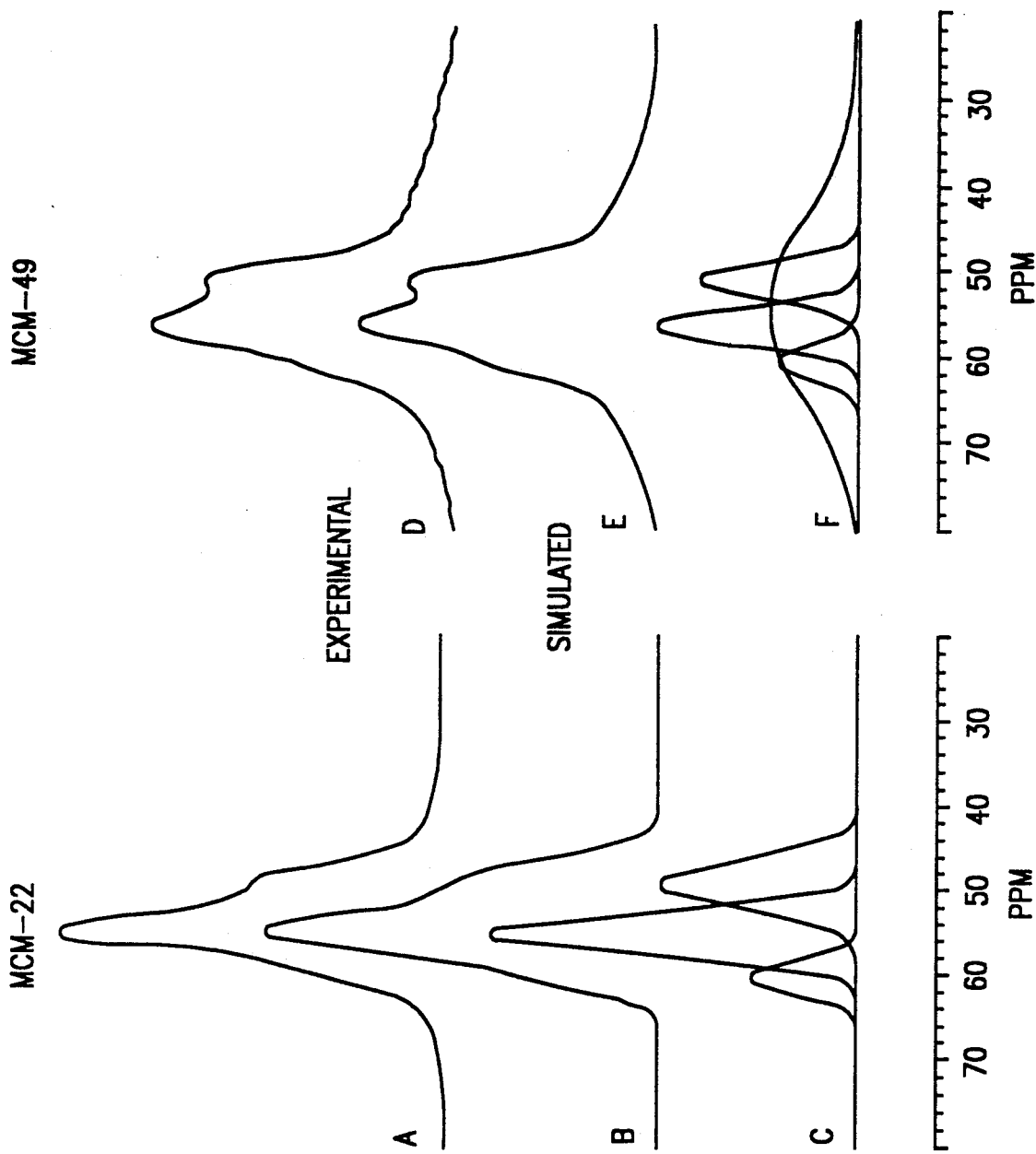
FIG. 8 compares the $^{27}Al$ MAS NMR spectra of calcined MCM-49 and calcined MCM-22.

As shown in FIG. 8, a difference between calcined MCM-49 and calcined MCM-22 can be demonstrated by $^{27}$Al MAS NMR. When calcined completely to remove the organic material used to direct its synthesis (FIG. 8D), MCM-49 exhibits a $^{27}$Al MAS NMR spectrum different from that of fully calcined MCM-22 (FIG. 8A). In each case, calcination is effected at 538° C. for 16 hours. The NMR spectra are obtained using a Bruker MSL-400 spectrometer at 104.25 MHz with 5.00 KHz spinning speed, 1.0 μs excitation pulses (solution $\pi/2=6$ μs), and 0.1S recycle times. The number of transients obtained for each sample is 2000, and the 27Al chemical shifts are referenced to a 1M aqueous solution of $Al(NO_3)_2$ at 0.0 ppm. As shown in FIGS. 8B and 8C, fully calcined MCM-22 exhibits a $^{27}$Al MAS NMR spectrum in which the $T_d$ Al region can be simulated as comprising 3 peaks centered at 61, 55, and 50 ppm having approximate relative areas of 10:50:40. In contrast, fully calcined MCM-49 exhibits a $^{27}$Al MAS NMR spectrum in which the $T_d$ Al region can be simulated as comprising the 3 peaks center at 61, 55, and 50 ppm but having approximate relative areas of 20:45:35, together with a fourth broad peak centered at 54 ppm (FIGS. 8E and 8F). Formation of the broad $T_d$ component does not appear to be dependent on the calcination environment (air or nitrogen). Calcined MCM-49 also exhibits distinctly different catalytic properties than calcined MCM-22.

MCM-49 can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, said reaction mixture having a composition, in terms of mole ratios of oxides, within the following ranges:

| Reactants | Useful | Preferred |
|---|---|---|
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one X component is present, at least one must be present such that the $YO_2/X_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum oxide has been added to the reaction mixture as a source of X, the $YO_2/Al_2O_3$ ratio must be less than about 35.

In the above synthesis method, the source of $YO_2$ must be comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-49 formation from the above mixture. Preferably, therefore, the $YO_2$, e.g. silica, source contains at least about 30 wt. % solid $YO_2$, e.g. silica, and more preferably at least about 40 wt. % solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

Crystallization of MCM-49 crystalline material can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of MCM-49 crystalline material will vary with the nature of the reaction mixture employed and the crystallization conditions.

Synthesis of MCM-49 may be facilitated by the presence of at least 0.01 percent, preferably 0.10 percent and still more preferably 1 percent, seed crystals (based on total weight) of crystalline product. Useful seed crystals include those having the structure of MCM-49.

The crystals prepared as above for use herein can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The MCM-49 olefin oligomerization catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of co-crystallization, exchanged into the composition to the extent a Group IIIB element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum ammine complex.

Zeolite MCM-49, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the oligomerization process of this invention, the zeolite MCM-49 crystals should be dehydrated, at least partially. This can be done by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

It may be desired to incorporate the MCM-49 with another material resistant to the temperatures and other conditions employed in organic conversion processes. Such materials include active and inactive materials and synthetic or naturally occurring zeolites as well as inorganic materials such as clays, silica and/or metal oxides such as, for example, alumina, titania or zirconia. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the MCM-49 crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the MCM-49 crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of zeolite MCM-49 may be increased by combining the as-synthesized MCM-49 with an alumina binder, converting the alumina-bound MCM-49 to the hydrogen form, (i.e., HMCM-49) and steaming the alumina-bound HMCM-49 composition under conditions sufficient to increase the stability of the catalyst. U.S. Pat. Nos. 4,663,492; 4,594,146; 4,522,929; and, 4,429,176, the entire disclosures of which are incorporated herein by reference, describe conditions for the steam stabilization of zeolite catalysts which can be utilized to steam-stabilize alumina-bound HMCM-49. The steam stabilization conditions include contacting the alumina bound HMCM-49 with, e.g., 5-100% steam at a temperature of at least about 300° C. (e.g., 300°-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

The oligomerization process of the present invention can be suitably carried out by contacting the olefinic feed with zeolite MCM-49 catalyst under olefin oligomerization conditions, e.g., a temperature of from about 50° C. to about 350° C., preferably from about 75° C. to about 125° C., a pressure of from about 100 psig to about 3000 psig, preferably from about 300 psig to about 2000 psig, and an LHSV of from about 0.1 to about 20 hr$^{-1}$, preferably from about 0.2 to about 10 hr$^{-1}$.

In order to more fully illustrate the nature of the invention and the manner of practicing same, the following examples are presented. In the examples, whenever sorption data are set forth for comparison of sorptive capacities for water, cyclohexane and/or n-hexane, they were Equilibrium Adsorption values determined as follows:

A weighed sample of the calcined adsorbant was contacted with the desired pure adsorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. The MCM-49 for use herein always exhibits Equilibrium Adsorption values of greater than about 10 wt. % for water vapor, greater than about 4.3 wt. %, usually greater than about 7 wt. % for cyclohexane vapor and greater than about 10 wt. % for n-hexane vapor. These vapor sorption capacities are a notable distinguishing feature of the presently used crystalline material.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

EXAMPLE 1

A 1 part quantity of $Al_2(SO_4)_3 \cdot xH_2O$ was dissolved in a solution containing 1.83 parts of 50% NaOH solution and 13 parts of $H_2O$. To this were added 1.78 parts of hexamethyleneimine (HMI) followed by 6.6 parts of amorphous silica precursor (46% solids). The mixture was thoroughly mixed until uniform.

The reaction mixture had the following composition in mole ratios:

| | | |
|---|---|---|
| $SiO_2/Al_2O_3$ | = | 30 |
| $OH^-/SiO_2$ | = | 0.25 |
| $Na/SiO_2$ | = | 0.43 |
| $HMI/SiO_2$ | = | 0.35 |
| $H_2O/SiO_2$ | = | 19.4 |

Figure 2:
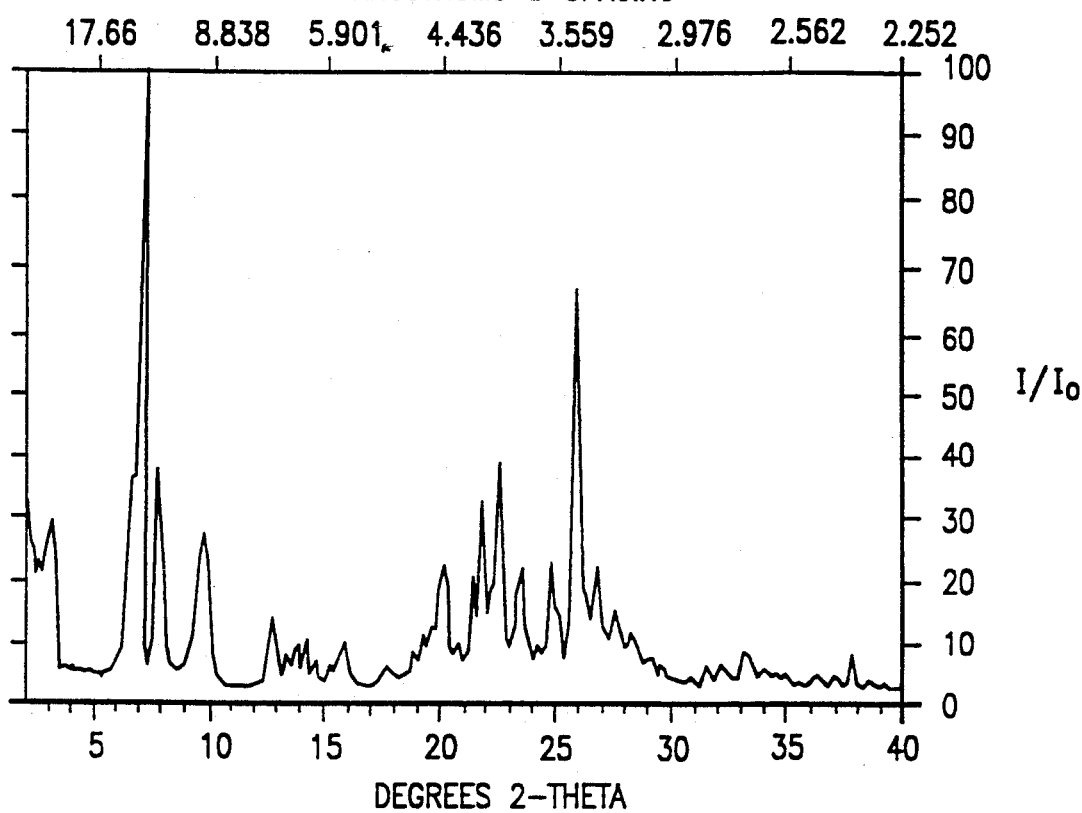
FIGS. 2–7 are X-ray diffraction patterns of the as-synthesized crystalline material products of Examples 1, 3, 5, 7, 8, and 10, respectively, hereinafter presented.

The mixture was crystallized in a stirred reactor at 150° C. for 4 days. The crystals were filtered, washed with water and dried at 120° C. A portion of the product was submitted for X-ray analysis and identified as the new crystalline material MCM-49. The material exhibited the X-ray powder diffraction pattern as shown in Table III and FIG. 2.

The chemical composition of the product was, in wt. %:

| | |
|---|---|
| N | 1.81 |
| Na | 0.38 |
| $Al_2O_3$ | 7.1 |
| $SiO_2$ | 72.8 |
| Ash | 79.2 |

The $SiO_2/Al_2O_3$ molar ratio of this product was 17.4.

The sorption capacities, after calcining for 6 hours at 538° C. were, in wt. %:

| | |
|---|---|
| Cyclohexane, 40 Torr | 4.4 |
| n-Hexane, 40 Torr | 12.8 |
| $H_2O$, 12 Torr | 11.1 |

A portion of the sample was calcined in air for 16 hours at 538° C. This material exhibited the X-ray diffraction pattern shown in Table IV.

TABLE III

| Degrees 2-Theta | Interplanar d-spacing (A) | $I/I_o$ |
|---|---|---|
| 3.2 | 27.5 | 11 |
| 6.75 | 13.09 | 36 sh |
| 7.08 | 12.49 | 100 |
| 7.88 | 11.23 | 40 |
| 9.81 | 9.02 | 24 |
| 12.79 | 6.92 | 13 |
| 13.42 | 6.60 | 5* |
| 13.87 | 6.38 | 6 |
| 14.24 | 6.22 | 7 |
| 14.64 | 6.05 | 4 |
| 15.24 | 5.81 | 2 |
| 15.81 | 5.61 | 8 |
| 17.72 | 5.01 | 2 |
| 18.91 | 4.69 | 4 |
| 19.27 | 4.61 | 5 |
| 20.09 | 4.42 | 19 |
| 20.83 | 4.26 | 6 |
| 21.48 | 4.14 | 15 |
| 21.78 | 4.08 | 29 |
| 22.22 | 4.00 | 12 |
| 22.59 | 3.94 | 36 |
| 23.56 | 3.78 | 19 |
| 24.87 | 3.58 | 21 |
| 25.10 | 3.55 | 6 |
| 25.89 | 3.44 | 80 |
| 26.32 | 3.39 | 7 |
| 26.81 | 3.33 | 17 |
| 27.57 | 3.24 | 11 |
| 28.36 | 3.15 | 7 |
| 29.03 | 3.08 | 3 |
| 29.50 | 3.03 | 2 |
| 31.47 | 2.842 | 3 |
| 32.16 | 2.784 | 3 |
| 33.26 | 2.694 | 6 |
| 34.08 | 2.631 | 2 |
| 34.83 | 2.576 | 1 |
| 36.25 | 2.478 | 2 |
| 36.96 | 2.432 | 2 |
| 37.72 | 2.385 | 7 | sh = Shoulder
* = Impurity peak

TABLE IV

| Degrees 2-Theta | Interplanar d-spacing (A) | $I/I_o$ |
|---|---|---|
| 3.4 | 26.0 | 6 |
| 6.96 | 12.69 | 45 sh |
| 7.15 | 12.37 | 100 |
| 7.97 | 11.09 | 58 |
| 9.97 | 8.87 | 49 |
| 12.88 | 6.88 | 10 |
| 13.50 | 6.56 | 3* |
| 14.34 | 6.18 | 26 |
| 14.76 | 6.00 | 8 |
| 15.30 | 5.79 | 1 |
| 15.96 | 5.55 | 13 |
| 17.84 | 4.97 | 1 |
| 19.03 | 4.66 | 3 |
| 19.34 | 4.59 | 2 |
| 19.67 | 4.51 | 2* |
| 20.26 | 4.38 | 10 |
| 21.18 | 4.20 | 3 |
| 21.59 | 4.12 | 10 |
| 21.88 | 4.06 | 17 |
| 22.40 | 3.97 | 8 |
| 22.72 | 3.91 | 28 |
| 23.74 | 3.75 | 16 |
| 24.73 | 3.60 | 3 |
| 24.98 | 3.57 | 10 |
| 25.23 | 3.53 | 5 |
| 26.00 | 3.43 | 57 |
| 26.98 | 3.30 | 12 |
| 27.81 | 3.21 | 12 |
| 28.64 | 3.12 | 7 |
| 29.14 | 3.06 | 2 |
| 29.69 | 3.01 | 2 |
| 31.62 | 2.830 | 3 |
| 32.28 | 2.773 | 3 |
| 33.38 | 2.685 | 6 |
| 34.43 | 2.605 | 2 |
| 34.98 | 2.565 | 2 |
| 36.39 | 2.469 | 1 |
| 37.09 | 2.424 | 2 |
| 37.86 | 2.377 | 4 | sh = Shoulder
* = Impurity peak

EXAMPLE 2

The calcined portion of the product of Example 1 was ammonium exchanged and calcined at 538° C. in air for 16 hours to provide the hydrogen form transformation product of the crystalline MCM-49. The Alpha test proved this material to have an Alpha Value of 291.

EXAMPLE 3

A 1.45 part quantity of sodium aluminate was added to a solution containing 1 part of 50% NaOH solution and 53.1 parts $H_2O$. A 5.4 part quantity of HMI was added, followed by 10.3 parts of Ultrasil, a precipitated spray-dried silica (about 90% $SiO_2$). The reaction mixture was thoroughly mixed and transferred to a stainless steel autoclave equipped with a stirrer.

The reaction mixture had the following composition in mole ratios:

| | | |
|---|---|---|
| $SiO_2/Al_2O_3$ | = | 25 |
| $OH^-/SiO_2$ | = | 0.19 |
| $Na/SiO_2$ | = | 0.19 |
| $HMI/SiO_2$ | = | 0.35 |
| $H_2O/SiO_2$ | = | 19.3 |

Figure 3:
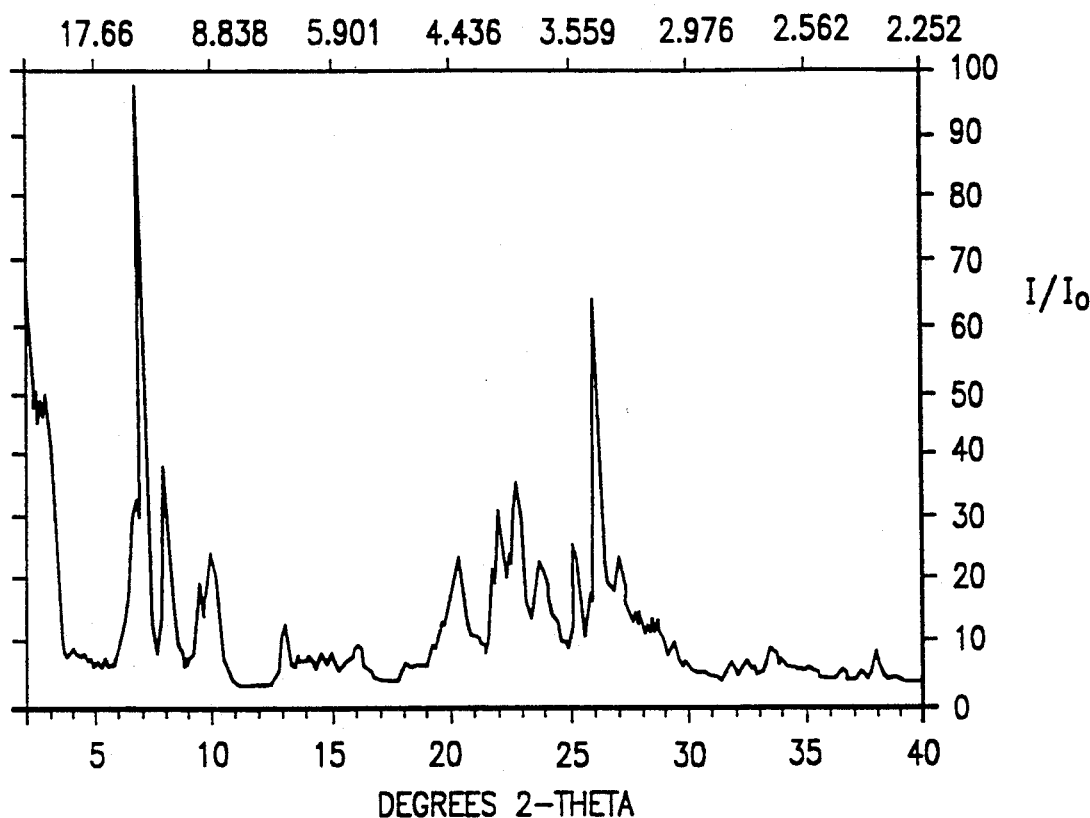

The mixture was crystallized with stirring at 150° C. for 8 days. The product was identified as poorly crystalline MCM-49 and had the X-ray pattern which appears in Table V and FIG. 3.

The chemical composition of the product was, in wt. %:

| | |
|---|---|
| N | 2.29 |
| Na | 0.19 |
| Al₂O₃ | 6.3 |
| SiO₂ | 71.0 |
| Ash | 77.9 |

The silica/alumina mole ratio of the product was 19.2.
The sorption capacities, after calcining for 16 hours at 538° C. were, in wt. %:

| | |
|---|---|
| Cyclohexane, 40 Torr | 9.9 |
| n-Hexane, 40 Torr | 14.6 |
| H₂O, 12 Torr | 15.1 |

A portion of the sample was calcined in air for 16 hours at 538° C. This material exhibited the X-ray diffraction pattern shown in Table VI.

TABLE V

| Degrees 2-Theta | Interplanar d-spacing (A) | I/I$_o$ |
|---|---|---|
| 3.0 | 29.3 | 8 |
| 3.9 | 22.8 | 2+ |
| 6.66 | 13.27 | 34 |
| 7.10 | 12.45 | 100 |
| 7.91 | 11.18 | 39 |
| 9.24 | 9.57 | 16* |
| 9.79 | 9.04 | 23 |
| 12 79 | 6.92 | 11 |
| 13.60 | 6.51 | 5 |
| 14.28 | 6.20 | 5 |
| 14.68 | 6.03 | 5 |
| 15.33 | 5.78 | 2 |
| 15.83 | 5.60 | 7 |
| 17.80 | 4.98 | 2 |
| 18.94 | 4.68 | 3 |
| 19.32 | 4.59 | 8 |
| 20.09 | 4.42 | 21 |
| 21.51 | 1.13 | 17 |
| 21.82 | 4.07 | 27 |
| 22.17 | 4.01 | 13 |
| 22.58 | 3.94 | 33 |
| 23.50 | 3.79 | 19 |
| 24.09 | 3.69 | 8* |
| 24.96 | 3.57 | 23 |
| 25.55 | 3.49 | 11* |
| 25.93 | 3.44 | 73 |
| 26.82 | 3.32 | 20 |
| 27.54 | 3.24 | 9 |
| 28.32 | 3.15 | 9** |
| 29.07 | 3.07 | 5** |
| 31.50 | 2.840 | 3 |
| 32.15 | 2.784 | 3 |
| 33.31 | 2.690 | 6 |
| 34.48 | 2 601 | 2 |
| 36.26 | 2.478 | 2 |
| 37.03 | 2.428 | 2 |
| 37.75 | 2.383 | 6 |

+ = Non-crystallographic MCM-49 peak
* = Impurity peak
** = May contain impurity peak

TABLE VI

| Degrees 2-Theta | Interplanar d-spacing (A) | I/I$_o$ |
|---|---|---|
| 3.9 | 22.8 | 6+ |
| 6.88 | 12.84 | 46 sh |
| 7.11 | 12 43 | 100 |
| 7.97 | 11.10 | 57 |
| 9.35 | 9 46 | 25* |
| 9.94 | 8.90 | 48 |
| 12.53 | 7.07 | 4* |
| 12.82 | 6.90 | 13 |
| 13.41 | 6.60 | 3* |
| 14.30 | 6.19 | 36 |
| 14.73 | 6.01 | 6 |
| 15.93 | 5.56 | 10 |
| 17.90 | 4.96 | 2 |
| 18.98 | 4.68 | 3 |
| 19.34 | 4.59 | 3 |
| 20.18 | 4.40 | 11 |
| 21.56 | 4.12 | 11 |
| 21.86 | 4.07 | 18 |
| 22.34 | 3.98 | 10 |
| 22.67 | 3.92 | 30 |
| 23.68 | 3.76 | 17 |
| 24.94 | 3.57 | 15 |
| 25.20 | 3.53 | 6* |
| 25.97 | 3.43 | 60 |
| 26.93 | 3.31 | 13 |
| 27.79 | 3.21 | 11 |
| 28.56 | 3.13 | 8** |
| 29.10 | 3.07 | 3** |
| 29.60 | 3.02 | 1 |
| 31.58 | 2.83 | 3 |
| 32.24 | 2.776 | 3 |
| 33.34 | 2.688 | 7 |
| 34.59 | 2.593 | 3 |
| 36.33 | 2.473 | 1 |
| 37.05 | 2.426 | 2 |
| 37.79 | 2.380 | 4 | sh = Shoulder
+ = Non-crystallographic MCM-49 peak
* = Impurity peak
** = May contain impurity peak

EXAMPLE 4

The calcined portion of the product of Example 3 was ammonium exchanged and calcined at 538° C. in air for 16 hours to provide the hydrogen form transformation product of the crystalline MCM-49. The Alpha Test proved this material to have an Alpha Value of 286.

EXAMPLE 5

A 10.5 part quantity of gallium oxide was added to a solution containing 1.0 part sodium aluminate, 3.05 parts 50% NaOH solution and 280 parts H20. A 25.6 part quantity of HMI was added followed by 56.6 parts of Ultrasil and 1.7 parts of MCM-22 seeds. The slurry was thoroughly mixed.

The composition of the reaction mixture in mole ratios:

| | | |
|---|---|---|
| SiO₂/Al₂O₃ | = | 138 |
| SiO₂/Ga₂O₃ | = | 17.9 |
| OH⁻/SiO₂ | = | 0.057 |
| Na/SiO₂ | = | 0.057 |
| HMI/SiO₂ | = | 0.30 |
| H₂O/SiO₂ | = | 18.4 |

Figure 4:
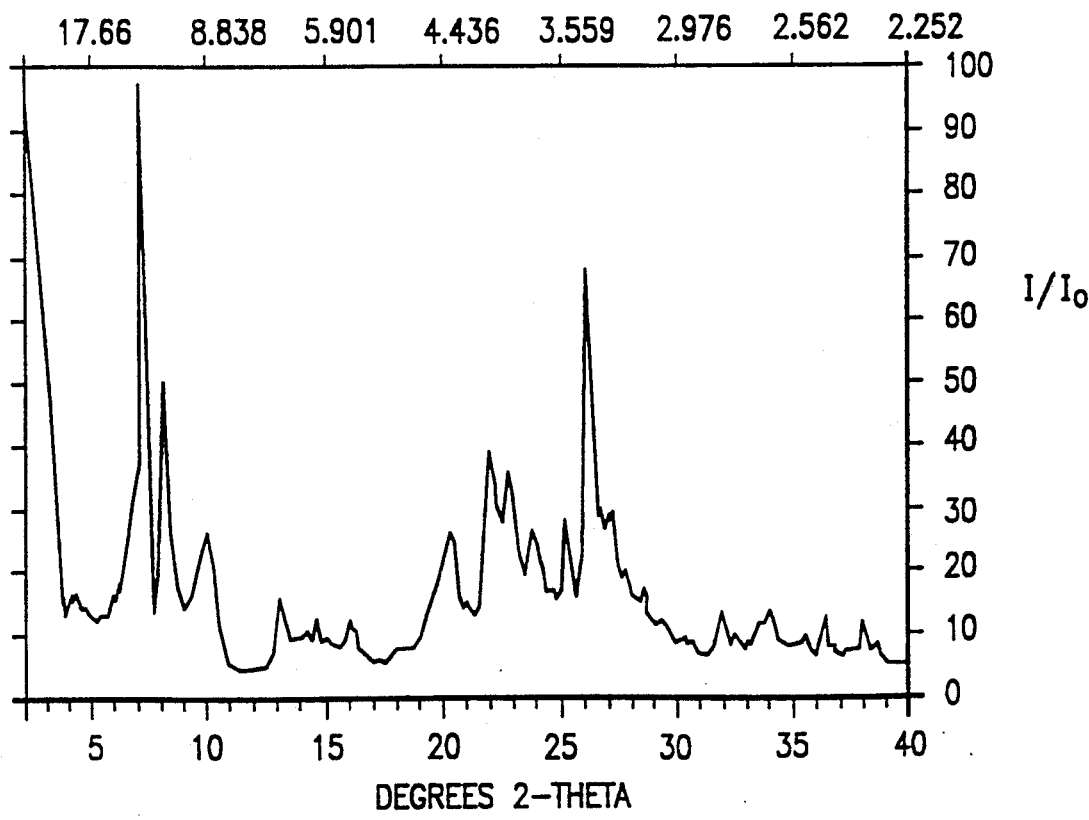

The mixture was crystallized with stirring at 150° C. for 10 days. The product was identified as poorly crystalline MCM-49 and had the X-ray pattern which appears in Table VII and FIG. 4.

The chemical composition of the product was, in wt. %:

| | |
|---|---|
| N | 1.89 |
| Na | 0.40 |
| Ga | 8.5 |
| Al₂O₃ | 0.81 |
| SiO₂ | 65.6 |

-continued

| | |
|---|---|
| Ash | 79.3 | with silica/alumina and silica/gallia molar ratios for the product of:

| | |
|---|---|
| $SiO_2/Al_2O_3$ | 138 |
| $SiO_2/Ga_2O_3$ | 17.9 |

The sorption capacities, after calcining for 3 hours at 538° C. were, in wt. %:

| | |
|---|---|
| Cyclohexane, 40 Torr | 13.3 |
| n-Hexane, 40 Torr | 11.3 |
| $H_2O$, 12 Torr | 12.3 |

A portion of the sample was calcined in air for 16 hours at 538° C. This material exhibited the X-ray diffraction pattern shown in Table VIII.

TABLE VII

| Degrees 2-Theta | Interplanar d-spacing (A) | $I/I_o$ |
|---|---|---|
| 3.9 | 22.8 | 6+ |
| 6.66 | 13.27 | 30 sh |
| 7.08 | 12.48 | 100 |
| 7.92 | 11.17 | 43 |
| 9.27 | 9.54 | 8* |
| 9.74 | 9.08 | 20 |
| 12.78 | 6.93 | 12 |
| 13.75 | 6.44 | 6 |
| 14.28 | 6.20 | 5 |
| 14.62 | 6.06 | 3 |
| 15.78 | 5.62 | 8 |
| 17.99 | 4.93 | 3 |
| 18.92 | 4.69 | 6 |
| 20.10 | 4.42 | 24 |
| 20.86 | 4.26 | 9 |
| 21.47 | 4.14 | 10 |
| 21.73 | 4.09 | 26 |
| 22.57 | 3.94 | 29 |
| 23.53 | 3.78 | 22 |
| 24.92 | 3.57 | 24 |
| 25.91 | 3.44 | 82 |
| 26.80 | 3.33 | 19 |
| 27.43 | 3.2 | 14 |
| 28.31 | 3.15 | 10 |
| 29.04 | 3.07 | 5 |
| 31.59 | 2.832 | 8 |
| 32.17 | 2.783 | 3 |
| 33.25 | 2.694 | 6 |
| 33.70 | 2.659 | 8* |
| 35.12 | 2.555 | 4* |
| 35.96 | 2.497 | 11* |
| 36.29 | 2.476 | 4 |
| 37.73 | 2.384 | 7 | sh = Shoulder
+ = Non-crystallographic MCM-49 peak
* = Impurity peak

TABLE VIII

| Degrees 2-Theta | Interplanar d-spacing (A) | $I/I_o$ |
|---|---|---|
| 3.9 | 22.8 | 11+ |
| 6.89 | 12.83 | 40 sh |
| 7.11 | 12.43 | 100 |
| 7.96 | 11.11 | 55 |
| 9.40 | 9.41 | 10* |
| 9.94 | 8.90 | 47 |
| 12.81 | 6.91 | 10 |
| 14.31 | 6.19 | 32 |
| 14.74 | 6.01 | 4 |
| 15.94 | 5.56 | 12 |
| 17.89 | 4.96 | <1 |
| 19.00 | 4.67 | 3 |
| 19.39 | 4.58 | 3 |
| 20.22 | 4.39 | 9 |
| 21.56 | 4.12 | 9 |
| 21.86 | 4.07 | 17 |
| 22.70 | 3.92 | 29 |
| 23.70 | 3.75 | 16 |
| 24.99 | 3.56 | 14 |
| 26.01 | 3.43 | 57 |
| 26.96 | 3.31 | 12 |
| 27.84 | 3.20 | 10 |
| 28.60 | 3.12 | 5 |
| 29.10 | 3.07 | 3 |
| 31.63 | 2.829 | 6 |
| 32.28 | 2.773 | 3 |
| 33.39 | 2.684 | 7 |
| 33.72 | 2.658 | 9* |
| 35.07 | 2.559 | 4* |
| 35.94 | 2.499 | 4* |
| 36.40 | 2.468 | 1 |
| 37.13 | 2.422 | 2 |
| 37.88 | 2.375 | 3 | sh = Shoulder
+ = Non-crystallographic MCM 49 peak
* = Impurity peak

EXAMPLE 6

The calcined portion of the product of Example 5 was ammonium exchanged and calcined at 538° C. in air for 16 hours to provide the hydrogen form transformation product of the crystalline MCM-49. The Alpha Test proved this material to have an Alpha Value of 64.

EXAMPLE 7

A solution containing 1 part of $Al_2(SO_4)_3 \cdot xH_2O$, 1,31 parts of 50% NaOH solution and 14.0 parts of $H_2O$ was prepared. To this were added 2.8 parts of Ultrasil precipitated silica followed by 1.48 parts of HMI. The reaction mixture was thoroughly mixed. The composition of the reaction mixture in mole ratios was:

| | | |
|---|---|---|
| $SiO_2/Al_2O_3$ | = | 25.5 |
| $OH^-/SiO_2$ | = | 0.15 |
| $Na/SiO_2$ | = | 0.39 |
| $HMI/SiO_2$ | = | 0.35 |
| $H_2O/SiO_2$ | = | 19.4 |

Figure 5:
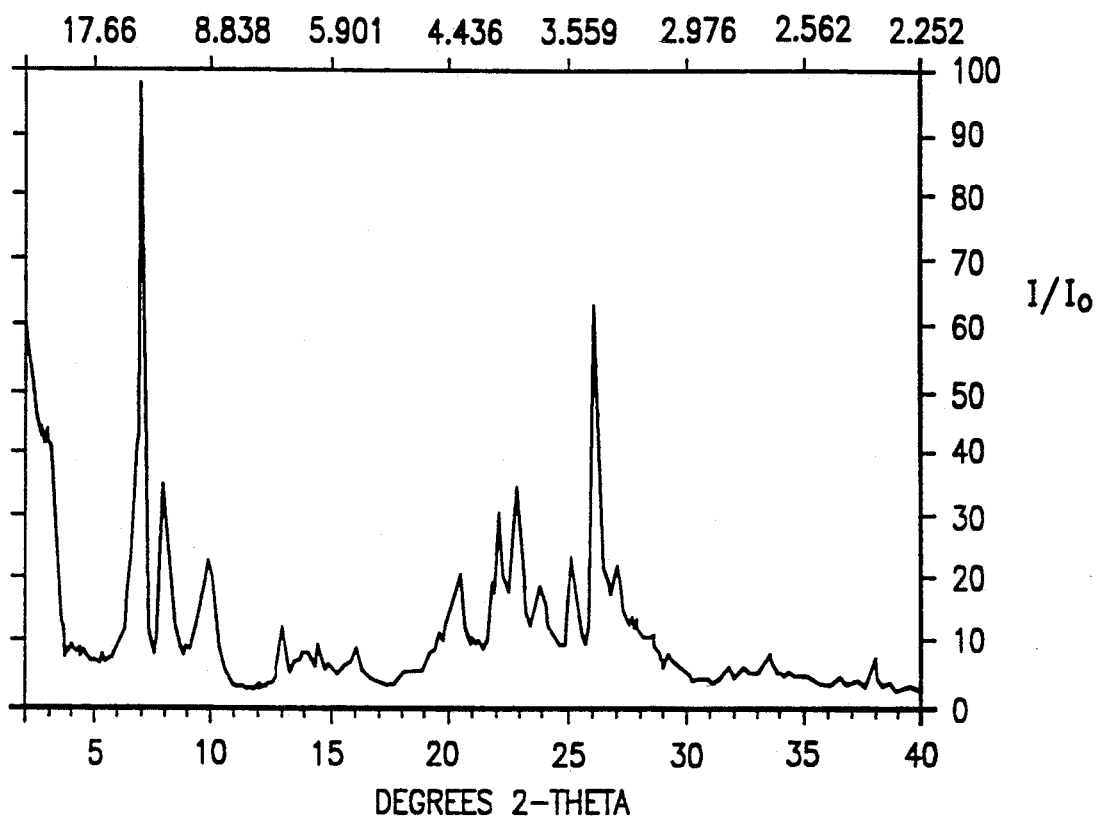

The mixture was crystallized for 5 days at 143° C. The product was washed, dried at 120° C. and identified by X-ray analysis as MCM-49. It exhibited an X-ray pattern as shown in Table IX and FIG. 5.

The sorption capacities, after calcining for 16 hours at 538° C. were, in wt. %:

| | |
|---|---|
| Cyclohexane, 40 Torr | 8.8 |
| n-Hexane, 40 Torr | 15.9 |
| $H_2O$, 12 Torr | 13.6 |

The chemical composition of the product was, in wt. %:

| | |
|---|---|
| N | 1.83 |
| Na | 0.27 |
| $Al_2O_3$ | 6.8 |
| $SiO_2$ | 73.8 |
| Ash | 80.5 |

The silica/alumina mole ratio of the product was 18.4.

The surface area of this material was measured to be 459 m²/g.

A portion of the sample was calcined in air for 16 hours at 538° C. This material exhibited the X-ray diffraction pattern shown in Table X.

TABLE IX

| Degrees 2-Theta | Interplanar d-spacing (A) | I/I$_o$ |
|---|---|---|
| 3.1 | 28.5 | 17 |
| 4.0 | 22.2 | 3+ |
| 6.73 | 13.14 | 43 sh |
| 7.08 | 12.48 | 100 |
| 7.92 | 11.16 | 42 |
| 9.69 | 9.13 | 23 |
| 12.80 | 6.91 | 13 |
| 13.76 | 6.44 | 7 |
| 14.27 | 6.20 | 6 |
| 14.65 | 6.05 | 3 |
| 15.85 | 5.59 | 7 |
| 17.82 | 4.98 | 2 |
| 18.92 | 4.69 | 3 |
| 19.32 | 4.59 | 8 |
| 20.13 | 4.41 | 20 |
| 21.48 | 4.14 | 12 |
| 21.82 | 4.07 | 31 |
| 22.56 | 3.94 | 36 |
| 23.59 | 3.77 | 18 |
| 24.91 | 3.57 | 22 |
| 25.91 | 3.44 | 79 |
| 26.74 | 3.33 | 20 |
| 27.61 | 3.23 | 7 |
| 28.25 | 3.16 | 8 |
| 29.14 | 3.06 | 3 |
| 31.48 | 2.842 | 3 |
| 32.16 | 2.783 | 3 |
| 33.26 | 2.694 | 6 |
| 33.85 | 2.648 | 3 sh |
| 34.72 | 2.584 | 2 |
| 36.26 | 2.478 | 2 |
| 37.00 | 2.429 | 2 |
| 37.73 | 2.384 | 7 | sh = Shoulder
+ = Non-crystallographic MCM-49 peak

TABLE X

| Degrees 2-Theta | Interplanar d-spacing (A) | I/I$_o$ |
|---|---|---|
| 3.9 | 22.8 | 6+ |
| 6.91 | 12.79 | 38 sh |
| 7.12 | 12.42 | 100 |
| 7.96 | 11.10 | 53 |
| 9.94 | 8.90 | 39 |
| 12.84 | 6.90 | 11 |
| 14.30 | 6.19 | 39 |
| 14.71 | 6.02 | 10 |
| 15.92 | 5.57 | 12 |
| 18.00 | 4.93 | 1 |
| 18.98 | 4.67 | 3 |
| 19.34 | 4.59 | 3 |
| 20.17 | 4.40 | 10 |
| 21.55 | 4.12 | 10 |
| 21.86 | 4.07 | 17 |
| 22.67 | 3.92 | 27 |
| 23.69 | 3.75 | 15 |
| 24.96 | 3.57 | 13 |
| 25.98 | 3.43 | 61 |
| 26.93 | 3.31 | 13 |
| 27.80 | 3.21 | 9 |
| 28.58 | 3.12 | 6 |
| 29.11 | 3.07 | 2 |
| 29.63 | 3.02 | 1 |
| 31.57 | 2.834 | 3 |
| 32.23 | 2.777 | 3 |
| 33.35 | 2.687 | 6 |
| 34.60 | 2.593 | 3 |
| 36.34 | 2.472 | 1 |
| 37.06 | 2.426 | 1 |

TABLE X-continued

| Degrees 2-Theta | Interplanar d-spacing (A) | I/I$_o$ |
|---|---|---|
| 37.83 | 2.378 | 5 | sh = Shoulder
+ = Non-crystallographic MCM-49 peak

EXAMPLE 8

A 2.24 part quantity of 45% sodium aluminate was added to a solution containing 1.0 part of 50% NaOH solution and 43.0 parts H$_2$O in an autoclave. An 8.57 part quantity of Ultrasil precipitated silica was added with agitation, followed by 4.51 parts of HMI.

The reaction mixture had the following composition, in mole ratios:

| | | |
|---|---|---|
| SiO$_2$/Al$_2$O$_3$ | = | 23 |
| OH$^-$/SiO$_2$ | = | 0.21 |
| Na/SiO$_2$ | = | 0.21 |
| HMI/SiO$_2$ | = | 0.35 |
| H$_2$O/SiO$_2$ | = | 19.3 |

Figure 6:
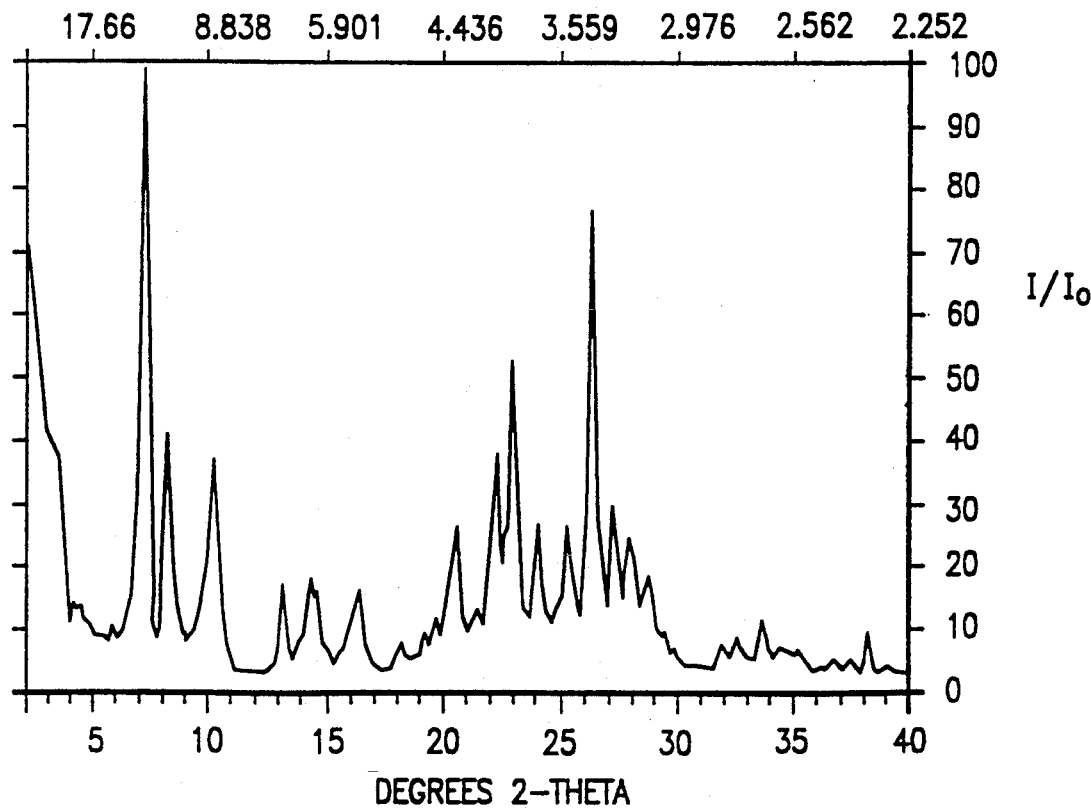

The mixture was crystallized at 150° C. for 84 hours with stirring. The product was identified as MCM-49 and had the X-tray pattern which appears in Table XI and FIG. 6.

The chemical composition of the product was, in wt. %:

| | |
|---|---|
| N | 1.70 |
| Na | 0.70 |
| Al$_2$O$_3$ | 7.3 |
| SiO$_2$ | 74.5 |
| Ash | 84.2 |

The silica/alumina mole ratio of the product was 17.3.

The sorption capacities, after calcining at 538° C. for 9 hours were, in wt. %:

| | |
|---|---|
| Cyclohexane, 40 Torr | 10.0 |
| n-Hexane, 40 Torr | 13.1 |
| H$_2$O, 12 Torr | 15.4 |

A portion of the sample was calcined in air for 3 hours at 538° C. This material exhibited the X-ray diffraction pattern shown in Table XII.

TABLE XI

| Degrees 2-Theta | Interplanar d-spacing (A) | I/I$_o$ |
|---|---|---|
| 3.1 | 28.5 | 18 |
| 3.9 | 22.8 | 7+ |
| 6.81 | 12.99 | 61 sh |
| 7.04 | 12.55 | 97 |
| 7.89 | 11.21 | 41 |
| 9.80 | 9.03 | 40 |
| 12.76 | 6.94 | 17 |
| 13.42 | 6.60 | 4* |
| 13.92 | 6.36 | 17 |
| 14.22 | 6.23 | 11 |
| 14.63 | 6.05 | 2 |
| 15.81 | 5.61 | 15 |
| 17.71 | 5.01 | 4 |
| 18.86 | 4.71 | 4 |
| 19.23 | 4.62 | 6 |
| 20.09 | 4.42 | 27 |
| 20.93 | 4.24 | 8 |
| 21.44 | 4.14 | 17 |
| 21.74 | 4.09 | 37 |

TABLE XI-continued

| Degrees 2-Theta | Interplanar d-spacing (A) | I/I$_o$ |
|---|---|---|
| 22.16 | 4.01 | 17 |
| 22.56 | 3.94 | 58 |
| 23.53 | 3.78 | 26 |
| 24.83 | 3.59 | 22 |
| 25.08 | 3.55 | 10 |
| 25.86 | 3.45 | 100 |
| 26.80 | 3.33 | 28 |
| 27.53 | 3.24 | 21 |
| 28.33 | 3.15 | 15 |
| 28.98 | 3.08 | 4 |
| 29.47 | 3.03 | 2 |
| 31.46 | 2.843 | 4 |
| 32.08 | 2.790 | 6 |
| 33.19 | 2.699 | 9 |
| 34.05 | 2.633 | 5 |
| 34.77 | 2.580 | 4 |
| 36.21 | 2.481 | 2 |
| 36.90 | 2.436 | 3 |
| 37.68 | 2.387 | 8 | sh = Shoulder
+ = Non-crystallographic MCM-49 peak
* = Impurity peak

TABLE XII

| Degrees 2-Theta | Interplanar d-spacing (A) | I/I$_o$ |
|---|---|---|
| 3.2 | 28.0 | 9+ |
| 3.9 | 22.8 | 7+ |
| 6.90 | 12.81 | 48 sh |
| 7.13 | 12.39 | 100 |
| 7.98 | 11.08 | 46 |
| 9.95 | 8.89 | 53 |
| 12.87 | 6.88 | 10 |
| 14.32 | 6.18 | 36 |
| 14.74 | 6.01 | 11 |
| 15.94 | 5.56 | 17 |
| 17.87 | 4.96 | 2 |
| 19.00 | 4.67 | 5 |
| 19.35 | 4.59 | 3 |
| 20.24 | 4.39 | 14 |
| 21.06 | 4.22 | 5 |
| 21.56 | 4.12 | 15 |
| 21.87 | 4.06 | 25 |
| 22.32 | 3.98 | 12 |
| 22.69 | 3.92 | 41 |
| 23.69 | 3.76 | 23 |
| 24.95 | 3.57 | 19 |
| 25.22 | 3.53 | 4 |
| 25.99 | 3.43 | 90 |
| 26.94 | 3.31 | 20 |
| 27.73 | 3.22 | 17 |
| 28.55 | 3.13 | 11 |
| 29.11 | 3.07 | 3 |
| 29.63 | 3.01 | 2 |
| 31.59 | 2.833 | 6 |
| 32.23 | 2.777 | 4 |
| 33.34 | 2.687 | 9 |
| 34.35 | 2.611 | 4 |
| 34.92 | 2.570 | 3 |
| 36.35 | 2.471 | 2 |
| 37.07 | 2.425 | 2 |
| 37.82 | 2.379 | 6 | sh = Shoulder
+ = Non-crystallographic MCM-49 peak

EXAMPLE 9

The calcined portion of the product of Example 8 was ammonium exchanged and calcined at 538° C. in air for 3 hours to provide the hydrogen form transformation product of the crystalline MCM-49. The Alpha Test proved this material to have an Alpha Value of 308.

EXAMPLE 10

Sodium aluminate comprising 40 wt. % Al$_2$O$_3$, 33 wt. % Na$_2$O, and 27 wt. % H$_2$O was added to a solution containing NaOH and H$_2$O in an autoclave. Ultrasil precipitated silica was then added with agitation, followed by aminocycloheptane (R) directing agent to form a reaction mixture.

This mixture had the following composition, in mole ratios:

| | |
|---|---|
| SiO$_2$Al$_2$O$_3$ = | 33.3 |
| OH$^-$/SiO$_2$ = | 0.18 |
| Na/SiO$_2$ = | 0.18 |
| R/SiO$_2$ = | 0.35 |
| H$_2$O/SiO$_2$ = | 18.8 |

Figure 7:
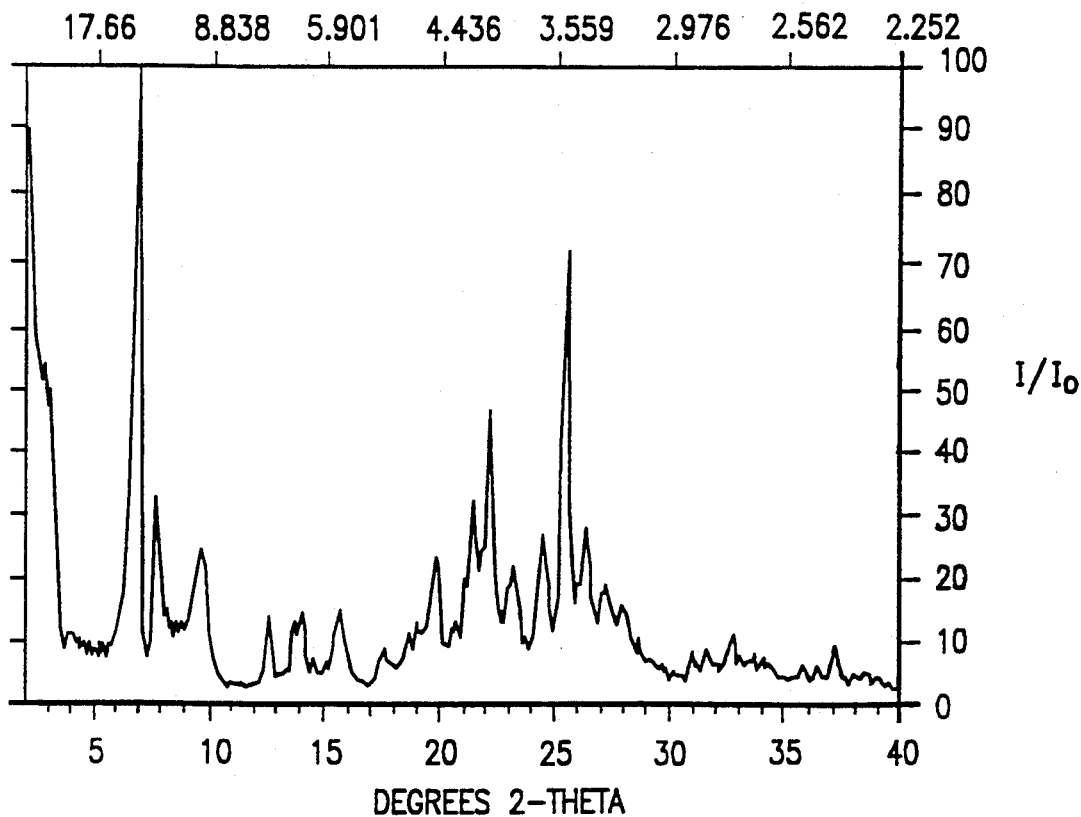

The mixture was crystallized at 143° C. for 192 hours with stirring. The product was identified as MCM-49 and had the X-ray pattern which appears in Table XIII and FIG. 7.

The chemical composition of the product was, in wt. %:

| | |
|---|---|
| N | 1.51 |
| Na | 0.83 |
| Al$_2$O$_3$ | 4.6 |
| SiO$_2$ | 74.2 |
| Ash | 79.2 |

The silica/alumina mole ratio of the product was 27.4.

The sorption capacities, after calcining at 538° C. for 9 hours were, in wt. %:

| | |
|---|---|
| Cyclohexane, 40 Torr | 7.5 |
| n-Hexane, 40 Torr | 14.0 |
| H$_2$O, 12 Torr | 13.5 |

TABLE XIII

| Degrees 2-Theta | Interplanar d-spacing (A) | I/I$_o$ |
|---|---|---|
| 4.1 | 21.4 | 1 |
| 6.87 | 12.87 | 41 |
| 7.14 | 12.38 | 100 |
| 7.98 | 11.09 | 26 |
| 9.88 | 8.95 | 18 |
| 12.85 | 6.89 | 14 |
| 14.00 | 6.33 | 10 |
| 14.31 | 6.19 | 11 |
| 14.74 | 6.01 | 2 |
| 15.88 | 5.58 | 13 |
| 17.79 | 4.99 | 4 |
| 18.95 | 4.68 | 6 |
| 19.34 | 4.59 | 7 |
| 20.20 | 4.40 | 18 |
| 21.06 | 4.22 | 7 |
| 21.51 | 4.13 | 12 |
| 21.82 | 4.07 | 27 |
| 22.63 | 3.93 | 46 |
| 23.60 | 3.77 | 19 |
| 24.90 | 3.58 | 25 |
| 25.14 | 3.54 | 7 |
| 25.92 | 3.44 | 90 |
| 26.82 | 3.32 | 26 |
| 27.66 | 3.22 | 13 |
| 28.43 | 3.14 | 12 |
| 29.03 | 3.08 | 4 |
| 29.45 | 3.03 | 3 |
| 31.51 | 2.839 | 4 |
| 32.15 | 2.784 | 5 |
| 33.24 | 2.695 | 8 |

TABLE XIII-continued

| Degrees 2-Theta | Interplanar d-spacing (A) | $I/I_o$ |
|---|---|---|
| 34.13 | 2.627 | 4 |
| 34.84 | 2.575 | 2 |
| 36.26 | 2.477 | 3 |
| 36.97 | 2.431 | 3 |
| 37.73 | 2.384 | 7 |

EXAMPLE 11

For comparison purposes, samples of ZSM-5, ZSM-23, ZSM-35, and MCM-22 catalysts were obtained. The ZSM-5, ZSM-23, and ZSM-35 catalysts were prepared as shown below. The MCM-22 was synthesized as in Example 1 of U.S. Pat. No. 4,954,325, incorporated herein by reference as to description of the zeolite and its synthesis. The X-ray diffraction pattern of the as-synthesized MCM-2 is presented in Table XIV. The X-ray diffraction pattern of the calcined form of this material (538° C. for 20 hours) is shown in Table XV below, and in FIG. 1 of U.S. Pat. No. 4,954,325.

ZSM-5

A solution containing 8.5 parts deionized water, 1.28 parts NaOH solution (50% by weight) and 1.0 part aluminum sulfate solution (47% aluminum sulfate, 8.1% $Al_2O_3$) was charged to an autoclave. After mixing, 0.008 part Daxad 23 (W. R. Grace) and 0.037 part ZSM-5 seeds (100% solids basis) were added. Then, 0.72 part brine solution (26% NaCl) was added followed by 4.13 parts DeGussa Ultrasil VN3SP precipitated silica and 0.46 part n-propylamine. The mixture was heated to 104°–110° C. with stirring and maintained there until crystallization was complete. The product was identified as ZSM-5 by X-ray diffraction. After flashing the organics, the material was cooled, washed, filtered, and dried at 150° C.

Eight parts of the ZSM-5 (100% solids basis), 1 part Ultrasil VN3SP (100% solids basis), 1 part Dupont Ludox HS-30 (100% basis), and 0.3 part NaOH (100% basis) were mulled with water and extruded to obtain a 1/16 inch quadrulobe extrudate. The extrudate was exchanged twice with 1N ammonium nitrate (5 cc/gm catalyst) for 1 hour at room temperature then dried at 120° C. The dried extrudate was calcined in nitrogen for 3 hours at 482° C., then 6 hours at 538° C. in air.

ZSM-23

Distilled water, 157 parts, was charged to an autoclave, followed by 2.33 parts NaOH solution (50% by weight), 1.0 part aluminum sulfate (17.2% $Al_2O_3$), and 1.0 part ZSM-23 seeds (100% solids basis). After mixing thoroughly, 26.4 parts of precipitated silica (PPG HiSil 233) and 9.33 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, filtered, washed, and dried at 120° C.

The dried ZSM-23, 65 parts, (100% solids basis), was combined with 20% precipitated silica (DeGussa Ultrasil VN3SP, 100% solids basis) and 15% colloidal silica (DuPont Ludox HS-30, 100% basis). Distilled water was added to give a mull mix which was extruded to produce a 1/16 inch cylindrical extrudate. After drying at 120° C., the extrudate was calcined in nitrogen at 538° C. for 2 hours and then in air for 3 hours. The calcined extrudate was then exchanged with a 1N ammonium nitrate solution (5 ml/g catalyst) at room temperature for 1 hour. The exchange was repeated 3 times, then the extrudate was rinsed with distilled water, dried at 120° C. and calcined in air at 538° C. for 3 hours.

ZSM-35

Distilled water, 9.42 parts, was charged to an autoclave, followed by 1.38 parts NaOH solution (50% by weight), 1.0 part aluminum sulfate (17.2 $Al_2O_3$). A quantity of 0.03 part of ZSM-35 seeds (100% basis) and 3.2 parts of PPG HiSil 233 precipitated silica were added with stirring, followed by 1.0 part of pyrrolidine. The autoclave was heated to 105° C. with stirring and maintained until crystallization was complete. The product was identified as ZSM-35 by X-ray diffraction. After flashing the pyrrolidine, the slurry was filtered, washed with distilled water, and dried at 120° C.

The dried material was calcined in nitrogen at 538° C. for 6 hours, then exchanged twice with 1N ammonium nitrate (5 ml/gm catalyst) for 1 hour at room temperature. After drying at 120° C., the material was heated to 510° C. in nitrogen, then air was introduced, and the material was calcined at 538° C. for 6 hours.

TABLE XIV

| Degrees 2-Theta | Interplanar d-spacing (A) | $I/I_o$ |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

TABLE XV

| Degrees 2-Theta | Interplanar d-spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 5.90 | 5.57 | 20 |
| 17.81 | 4.98 | 5 |
| 9.08 | 4.65 | 2 |
| 20.20 | 4.40 | 20 |
| 20.91 | 4.25 | 5 |
| 21.59 | 4.12 | 20 |

TABLE XV-continued

| Degrees 2-Theta | Interplanar d-spacing (A) | $I/I_o$ |
|---|---|---|
| 21.92 | 4.06 | 13 |
| 22.67 | 3.92 | 30 |
| 23.70 | 3.75 | 13 |
| 25.01 | 3.56 | 20 |
| 26.00 | 3.43 | 100 |
| 26.96 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLES 12-26

Fifteen experiments were conducted to compare olefin oligomerization catalysts, i.e., those of Example 11 above, with the MCM-49 used here.

For each experiment, 6.2 g of each catalyst were sized to 20/40 mesh, mixed with 5 g of 20/40 mesh sand, and loaded into continuous flow, ⅜" o.d. micro-reactors. The experiments were conducted on a single-pass basis. The feed used was a 60/40 mole % propylene/propane mixture. The WHSV used was based on zeolite content in the catalyst. Products were analyzed by gas chromatography. Reaction temperature was adjusted to provide 90+% propylene conversion in each experiment. Data for the second MCM-22 run (Example 16) was measured after 1 day on stream.

Operating conditions and the data obtained for the 15 experiments are given in Table XVI.

lysts required a substantially higher temperature (from about 75° to 200° C. higher) than the MCM-49 catalyst. Further, the second column of MCM-22 data (Example 16), taken after only 1 day on stream, shows a 25% drop in propylene conversion at constant temperature for that catalyst. This clearly demonstrates that MCM-49 is significantly more active than the other catalysts for the process of olefin oligomerization.

Further as demonstrated above, the propylene oligomer products from MCM-49 catalyst have high methyl branching (methyls/$C_{12}$>2.1) with more than 50% of the products in the $C_4$-$C_{10}$ gasoline range. Within that range, the product selectivity is dominated by $C_7$-$C_9$ gasoline. Thus, the products of this process are valuable for etherification and as high octane gasoline.

What is claimed is:

1. A process for converting olefin feedstock to higher molecular weight hydrocarbon product which comprises contacting a feedstock containing at least one oligomerizable olefin with an olefin oligomerization catalyst composition under olefin oligomerization conditions to provide said higher molecular weight hydrocarbon product, said olefin oligomerization catalyst comprising an active form of synthetic porous crystalline material characterized by an X-ray diffraction pattern including values substantially as follows:

| Interplanar d-Spacing (A) | Relative Intensity |
|---|---|
| 13.15 ± 0.26 | w-s (shoulder) |
| 12.49 ± 0.24 | vs |
| 11.19 ± 0.22 | m-s |
| 6.43 ± 0.12 | w |
| 4.98 ± 0.10 | w |
| 4.69 ± 0.10 | w |
| 3.44 ± 0.07 | vs |

TABLE XVI

| Example | 12 | 13 | 14 | 15 | 16 | 17 | 18 | 19 |
|---|---|---|---|---|---|---|---|---|
| Catalyst | MCM-49 | MCM-49 | MCM-49 | MCM-22 | MCM-22 | ZSM-5/SiO$_2$ | ZSM-5/SiO$_2$ | ZSM-5/SiO$_2$ |
| Reaction Temp, °C. | 65 | 75 | 105 | 280 | 280 | 155 | 165 | 175 |
| Pressure, psig | 1000 | 1000 | 1000 | 1000 | 1000 | 800 | 800 | 800 |
| WHSV (zeolite), hr$^{-1}$ | 0.49 | 0.51 | 0.52 | 0.52 | 0.53 | 0.51 | 0.55 | 0.50 |
| Product Analysis, wt. % | | | | | | | | |
| $C_4$-$C_7$ | 14.78 | 10.92 | 5.39 | 16.24 | 17.75 | 4.87 | 6.25 | 5.36 |
| $C_7$-$C_{10}$ | 52.13 | 47.67 | 48.02 | 43.93 | 56.93 | 49.37 | 44.09 | 33.01 |
| $C_{10}$-$C_{13}$ | 20.39 | 22.16 | 21.19 | 21.02 | 16.03 | 29.96 | 30.45 | 31.44 |
| $C_{13}$-$C_{16}$ | 9.52 | 11.17 | 14.89 | 9.62 | 5.54 | 10.66 | 12.45 | 16.93 |
| $C_{16}$-$C_{19}$ | 2.60 | 3.98 | 6.23 | 5.78 | 2.74 | 0.77 | 4.31 | 7.47 |
| $C_{19}$-$C_{22}$ | 0.58 | 1.59 | 2.49 | 2.72 | 0.26 | 0.40 | 1.36 | 3.39 |
| $C_{22}$-$C_{25}$ | — | 1.19 | 0.98 | 0.66 | 0.23 | 0.32 | 0.50 | 1.32 |
| $C_{24}$+ | — | 1.32 | 0.82 | 0.03 | 0.52 | 0.30 | 0.59 | 1.08 |
| Propylene Conversion, wt. % | 87.42 | 91.76 | 99.54 | 95.34 | 71.02 | 83.27 | 88.15 | 97.01 |
| Methyls/$C_{12}$ | 2.29 | 2.30 | 2.13 | >2.0 | >2.0 | — | — | — |

| Example | 20 | 21 | 22 | 23 | 24 | 25 | 26 |
|---|---|---|---|---|---|---|---|
| Catalyst | ZSM-23/SiO$_2$ | ZSM-23/SiO$_2$ | ZSM-23/SiO$_2$ | ZSM-35 | ZSM-35 | ZSM-35 | ZSM-35 |
| Reaction Temp, °C. | 145 | 155 | 170 | 120 | 130 | 150 | 170 |
| Pressure, psig | 1000 | 1000 | 1000 | 1000 | 1000 | 1000 | 1000 |
| WHSV (zeolite), hr$^{-1}$ | 0.48 | 0.49 | 0.49 | 0.49 | 0.49 | 0.49 | 0.49 |
| Product Analysis, wt. % | | | | | | | |
| $C_4$-$C_7$ | 20.79 | 22.31 | 15.71 | 34.92 | 27.75 | 18.85 | 15.28 |
| $C_7$-$C_{10}$ | 53.68 | 51.06 | 42.94 | 46.12 | 46.60 | 45.76 | 38.96 |
| $C_{10}$-$C_{13}$ | 17.04 | 17.87 | 19.53 | 15.83 | 19.48 | 24.63 | 25.59 |
| $C_{13}$-$C_{16}$ | 5.09 | 5.43 | 10.21 | 1.90 | 3.26 | 7.15 | 12.88 |
| $C_{16}$-$C_{19}$ | 2.20 | 2.06 | 7.09 | 0.76 | 1.68 | 2.48 | 4.80 |
| $C_{19}$-$C_{22}$ | 0.70 | 0.84 | 1.05 | 0.32 | 1.22 | 0.84 | 2.12 |
| $C_{22}$-$C_{25}$ | 0.50 | 0.44 | 2.23 | 0.14 | — | 0.27 | 0.37 |
| $C_{24}$+ | — | — | 1.23 | 0.01 | — | 0.01 | — |
| Propylene Conversion, wt. % | 53.90 | 69.64 | 93.34 | 76.16 | 87.25 | 92.6 | 101.22 |
| Methyls/$C_{12}$ | 1.84 | 1.87 | 1.91 | 2.30 | 2.24 | 2.26 | 2.15 |

These results show that to achieve 90+% propylene conversion in this oligomerization process, all the cata-

| Interplanar d-Spacing (A) | Relative Intensity |
|---|---|
| 3.24 ± 0.06 | w | and having a composition comprising the molar relationship $$X_2O_3:(n)YO_2,$$

wherein n is less than about 35, X is a trivalent element and Y is a tetravalent element.

2. The process of claim 1 wherein n is from about 2 to less than about 35.

3. The process of claim 3 wherein n is from about 10 to less than about 35.

4. The process of claim 1 wherein X is a trivalent element selected from the group consisting of aluminum, boron, iron, gallium, and mixtures thereof, and Y is a tetravalent element selected from the group consisting of silicon, titanium, germanium, and mixtures thereof.

5. The process of claim 4 wherein X comprises aluminum and Y comprises silicon.

6. The process of claim 1 wherein said synthetic porous crystalline MCM-49 has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

7. The process of claim 1 wherein said synthetic porous crystalline MCM-49 has been thermally treated at a temperature up to about 925° C in the presence or absence of steam.

8. The process of claim 6 wherein said synthetic porous crystalline MCM-49 has been thermally treated at a temperature up to about 925° C. in the presence or absence of steam.

9. The process of claim 1 wherein said catalyst comprises a material matrix.

10. The process of claim 9 wherein said matrix material comprises alumina, silica, zirconia, titania, or mixture thereof.

11. The process of claim 9 wherein the catalyst is provided in the form of extrudate, beads or fluidizable microspheres.

12. The process of claim 1 wherein the oligomerizable olefin possesses from 2 to 16 carbon atoms.

13. The process of claim 1 wherein said feedstock comprises propylene.

14. The process of claim 1 wherein said feedstock comprises an FCC light olefin stream.

15. The process of claim 1 wherein the oligomerization conditions include a temperature of from about 50° C. to about 350° C., a pressure of from 100 to about 3000 psig, and an LHSV of from about 0.1 to about 20 hr$^{-1}$.

16. The process of claim 1 wherein the oligomerization conditions include a temperature of from about 75° C. to about 125° C., a pressure of from about 300 to about 2000 psig, and an LHSV of from about 0.2 to about 10 hr$^{-1}$.

* * * * *

UNITED STATES PATENT AND TRADEMARK OFFICE
CERTIFICATE OF CORRECTION

PATENT NO. : 5,264,643
DATED : November 23, 1993
INVENTOR(S) : F.T. DiGuiseppi et al.

It is certified that error appears in the above-identified patent and that said Letters Patent is hereby corrected as shown below:

Col. 24, claim 1, Table, "4.69 ± 0.10" should be
--4.69 ± 0.09--.

Col. 25, claim 3, line 15, "claim 3" should be
--claim 2--.

Signed and Sealed this

Seventeenth Day of May, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,264,643
DATED : November 23, 1993
INVENTOR(S) : F.T. DiGuiseppi, et al It is certified that error appears in the above-indentified patent and that said Letters Patent is hereby corrected as shown below:

Col. 24, claim 1, Table, "4.69 ± 0.10" should be --4.69 ± 0.09--.

Col. 25, claim 3, line 15, "claim 3" should be --claim 2--.

Signed and Sealed this

Fifth Day of July, 1994

Attest:

BRUCE LEHMAN

Attesting Officer

Commissioner of Patents and Trademarks